(12) United States Patent
Burnett et al.

(10) Patent No.: US 10,709,789 B2
(45) Date of Patent: *Jul. 14, 2020

(54) LOW PROTEIN PERCENTAGE GELLING COMPOSITIONS

(71) Applicant: Keratin Biosciences, Inc., Winston-Salem, NC (US)

(72) Inventors: Luke Burnett, Winston-Salem, NC (US); Elizabeth Kneller, Winston-Salem, NC (US); Seth Tomblyn, Belmont, NC (US)

(73) Assignee: Keranetics, Inc., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/371,629

(22) Filed: Apr. 1, 2019

(65) Prior Publication Data

US 2019/0351063 A1 Nov. 21, 2019

Related U.S. Application Data

(60) Continuation of application No. 15/619,615, filed on Jun. 12, 2017, now Pat. No. 10,279,045, which is a division of application No. 14/238,672, filed as application No. PCT/US2012/051215 on Aug. 16, 2012, now Pat. No. 9,700,631.

(60) Provisional application No. 61/524,549, filed on Aug. 17, 2011.

(51) Int. Cl.
| | | |
|---|---|---|
| *A61K 38/00* | (2006.01) | |
| *A61K 47/42* | (2017.01) | |
| *C08J 3/075* | (2006.01) | |
| *A61L 27/22* | (2006.01) | |
| *A61L 27/52* | (2006.01) | |

(52) U.S. Cl.
CPC ............ *A61K 47/42* (2013.01); *A61L 27/227* (2013.01); *A61L 27/52* (2013.01); *C08J 3/075* (2013.01); *C08J 2300/14* (2013.01); *C08J 2399/00* (2013.01)

(58) Field of Classification Search
None
See application file for complete search history.

(56) References Cited

U.S. PATENT DOCUMENTS

| | | | |
|---|---|---|---|
| 2,993,794 | A | 7/1961 | Moshy |
| 3,464,825 | A | 9/1969 | Anker |
| 4,570,629 | A | 2/1986 | Widra |
| 5,006,467 | A | 4/1991 | Kusano et al. |
| 5,047,249 | A | 9/1991 | Rothman et al. |
| 5,100,783 | A | 3/1992 | Dean, Jr. et al. |
| 5,153,132 | A | 10/1992 | Goodwin et al. |
| 5,300,285 | A | 4/1994 | Halloran et al. |
| 5,320,796 | A | 6/1994 | Harashima et al. |
| 5,358,935 | A | 10/1994 | Smith et al. |
| 5,512,474 | A | 4/1996 | Clapper et al. |
| 5,634,945 | A | 6/1997 | Pernia et al. |
| 5,636,643 | A | 6/1997 | Argenta et al. |
| 5,645,081 | A | 7/1997 | Argenta et al. |
| 5,651,960 | A | 7/1997 | Chan et al. |
| 5,651,966 | A | 7/1997 | Read et al. |
| 5,679,819 | A | 10/1997 | Jones et al. |
| 5,707,972 | A | 1/1998 | Shimizu |
| 5,763,583 | A | 6/1998 | Arai et al. |
| 5,852,024 | A | 12/1998 | Pines et al. |
| 5,883,078 | A | 3/1999 | Seelich et al. |
| 5,902,608 | A | 5/1999 | Read et al. |
| 5,932,552 | A | 8/1999 | Blanchard et al. |
| 5,948,432 | A | 9/1999 | Timmons et al. |
| 5,972,335 | A | 10/1999 | Ferguson et al. |
| 6,110,487 | A | 8/2000 | Timmons et al. |
| 6,124,265 | A | 9/2000 | Timmons et al. |
| 6,159,495 | A | 12/2000 | Timmons et al. |
| 6,159,496 | A | 12/2000 | Blanchard et al. |
| 6,165,496 | A | 12/2000 | Timmons et al. |
| 6,251,379 | B1 | 6/2001 | Omura et al. |
| 6,268,454 | B1 | 7/2001 | Song et al. |
| 6,270,791 | B1 | 8/2001 | Van Dyke et al. |
| 6,270,793 | B1 | 8/2001 | Van Dyke et al. |
| 6,274,155 | B1 | 8/2001 | Van Dyke et al. |
| 6,274,163 | B1 | 8/2001 | Blanchard et al. |
| 6,316,598 | B1 | 11/2001 | Van Dyke et al. |
| 6,371,984 | B1 | 4/2002 | Van Dyke et al. |
| 6,379,690 | B2 | 4/2002 | Blanchard et al. |
| 6,432,435 | B1 | 8/2002 | Timmons et al. |
| 6,461,628 | B1 | 10/2002 | Blanchard et al. |
| 6,544,548 | B1 | 4/2003 | Siller-Jackson et al. |
| 6,696,073 | B2 | 2/2004 | Boyce et al. |
| 6,746,836 | B1 | 6/2004 | Widra |
| 6,783,546 | B2 | 8/2004 | Zucherman et al. |
| 6,808,927 | B2 | 10/2004 | Greenfield et al. |

(Continued)

FOREIGN PATENT DOCUMENTS

| | | |
|---|---|---|
| CN | 102120753 | 7/2011 |
| GB | 351600 | 7/1931 |

(Continued)

OTHER PUBLICATIONS

Guzman et. al. Biomaterials, 32 (2011) 8205-8217).*
Hill et. al. Biomaterials, 31 (2010) 585-593).*
American Heritage Dictionary, White. Retrieved online at: https://web.archive.org/web/20170714192941/https://ahdictionary.com/word/- search.html?q=white. 4 pages, (2017).
Bamstead International, Lab-Line®. Max Q 4000, Incubated & Refrigerated Shakers, Model No. SHKA4000, SHKA4000-1CE, SHKA4000-5, SHKA4000-6CE, SHKA4000-7, SHKA4000-8CE, SHKE4000, SHKE4000-1CE, SHKE4000-5, SHKE4000-6CE, SHKE4000-7, SHKE4000-8CE. Operation Manual, Manual No. 057-287-00, Rev. E, ECN 19157. 33 pages, retrieved on Sep. 6, 2017.

(Continued)

*Primary Examiner* — Jeanette M Lieb
(74) *Attorney, Agent, or Firm* — Massey Law, PLLC

(57) ABSTRACT

Described herein are low protein concentration gelling compositions comprising keratin proteins.

25 Claims, 4 Drawing Sheets

(56) References Cited

U.S. PATENT DOCUMENTS

| | | |
|---|---|---|
| 6,825,323 B2 | 11/2004 | Hess |
| 6,833,488 B2 | 12/2004 | Bucevschi et al. |
| 6,858,383 B2 | 2/2005 | Sabbadini |
| 6,869,445 B1 | 3/2005 | Johnson |
| 7,148,327 B2 | 12/2006 | Kelly et al. |
| 7,439,012 B2 | 10/2008 | Van Dyke |
| 7,892,572 B2 | 2/2011 | Peplow et al. |
| 7,892,573 B2 | 2/2011 | Van Dyke |
| 8,021,830 B2 | 9/2011 | Van Dyke |
| 8,258,093 B2 | 9/2012 | Van Dyke |
| 8,273,702 B2 | 9/2012 | Van Dyke |
| 8,299,013 B2 | 10/2012 | Van Dyke |
| 9,700,631 B2 | 7/2017 | Burnett et al. |
| 9,827,245 B2 | 11/2017 | Tomblyn et al. |
| 2001/0021389 A1 | 9/2001 | Starling et al. |
| 2001/0047082 A1 | 11/2001 | Van Dyke et al. |
| 2002/0192196 A1 | 12/2002 | Allen-Hoffmann |
| 2003/0049266 A1 | 3/2003 | Fearon et al. |
| 2003/0109587 A1 | 6/2003 | Mori |
| 2003/0204037 A1 | 10/2003 | Van Dyke |
| 2003/0228353 A1 | 12/2003 | Cowsar |
| 2004/0011052 A1 | 1/2004 | Van Dyke et al. |
| 2004/0062793 A1 | 4/2004 | Dyke |
| 2004/0076599 A1 | 4/2004 | Siller-Jackson et al. |
| 2004/0078090 A1 | 4/2004 | Binette et al. |
| 2004/0120910 A1 | 6/2004 | Dyke |
| 2004/0267362 A1 | 12/2004 | Hwang et al. |
| 2005/0058686 A1 | 3/2005 | Van Dyke |
| 2005/0084542 A1 | 4/2005 | Rosenberg et al. |
| 2005/0169963 A1 | 8/2005 | Van Dyke et al. |
| 2006/0051732 A1 | 3/2006 | Van Dyke |
| 2006/0140889 A1 | 6/2006 | Kloutzager et al. |
| 2007/0050387 A1 | 3/2007 | Van Dyke |
| 2007/0166348 A1 | 7/2007 | Van Dyke |
| 2007/0207111 A1 | 9/2007 | Nomura et al. |
| 2007/0208134 A1 | 9/2007 | Hunter et al. |
| 2007/0298070 A1 | 12/2007 | Van Dyke |
| 2008/0003676 A1 | 1/2008 | Sheridan et al. |
| 2008/0038327 A1 | 2/2008 | Kelly et al. |
| 2008/0274165 A1 | 11/2008 | Van Dyke |
| 2009/0004242 A1 | 1/2009 | Van Dyke |
| 2009/0017001 A1 | 1/2009 | Van Dyke |
| 2009/0017031 A1 | 1/2009 | Fung |
| 2009/0047260 A1 | 2/2009 | Van Dyke |
| 2009/0209738 A1 | 8/2009 | Cranston et al. |
| 2010/0197021 A1 | 8/2010 | Van Dyke |
| 2011/0137329 A1 | 6/2011 | Dyke |
| 2011/0142910 A1 | 6/2011 | Van Dyke |
| 2011/0217285 A1 | 9/2011 | Van Dyke et al. |
| 2011/0217356 A1 | 9/2011 | Van Dyke et al. |
| 2011/0300193 A1 | 12/2011 | Van Dyke |
| 2012/0219667 A1 | 8/2012 | Kelly et al. |
| 2012/0276188 A1 | 11/2012 | Barrows |
| 2015/0011659 A1 | 1/2015 | Burnett et al. |
| 2015/0080552 A1 | 3/2015 | Burnett et al. |
| 2016/0324750 A1 | 11/2016 | Burnett et al. |
| 2017/0051027 A1 | 2/2017 | Van Dyke et al. |

FOREIGN PATENT DOCUMENTS

| | | |
|---|---|---|
| WO | 1999/26570 | 6/1999 |
| WO | 1999/26595 | 6/1999 |
| WO | 1999/51175 | 10/1999 |
| WO | 2000/76437 | 12/2000 |
| WO | 2001/19283 | 3/2001 |
| WO | 2001/19305 | 3/2001 |
| WO | 2001/64033 | 9/2001 |
| WO | 2002/45508 | 6/2002 |
| WO | 2003/011894 | 2/2003 |
| WO | 2003/064449 | 8/2003 |
| WO | 2003/086491 | 10/2003 |
| WO | 2004/011052 | 2/2004 |
| WO | 2007/001339 | 1/2007 |
| WO | 2007/050387 | 5/2007 |
| WO | 2007/095151 | 8/2007 |
| WO | 2007/098053 | 8/2007 |
| WO | 2007/098114 | 8/2007 |
| WO | 2008/070091 | 6/2008 |
| WO | 2008/130607 | 10/2008 |
| WO | 2010/093882 | 8/2010 |
| WO | 2011/109808 | 9/2011 |
| WO | 2011/112575 | 9/2011 |
| WO | 2012/068376 | 5/2012 |
| WO | 2013/025928 | 2/2013 |
| WO | 2013/025940 | 2/2013 |
| WO | 2013/025941 | 2/2013 |
| WO | 2016/100476 | 6/2016 |

OTHER PUBLICATIONS

BASF, Sodium sulfite by BASF. 1 page, retreived Oct. 4, 2017.
Business Wire, Thermo Electron and Fisher Scientific to Combine in Industry-Transforming Transaction. Fisher Scientific International Inc. and Thermo Electron Corporation. 6 pages, May 8, 2006.
ChemPages, Mechanical Mixing. ChemPages Laboratory Resources. Retrieved online at: http://faculty.sdmiramar.edu/fgarces/labmatters/chemtech/modules/mixing/mixmech.htm. 3 pages, (2018).
De Guzman et al., Mechanical and biological properties of keratose biomaterials. Biomaterials. Nov. 2011;32(32):8205-17.
Hill et al., Some properties of keratin biomaterials: kerateines. Biomaterials. Feb. 2010;31(4):585-93.
Millipore, Protein Concentration and Diafiltration by Tangential Flow Filtration. Millipore Corporation, 24 pages, (2003).
Nakamura et al., A rapid extraction procedure of human hair proteins and identification of phosphorylated species. Biol Pharm Bull. May 2002;25(5):569-72.
Pall Laboratory, Tangential Flow Filtration. Retrieved online at: https://web.archive.org/web/20170611014224/https://laboratory.pall.com/en/tangential-flow-filtration.html. 11 pages, (2017).
Peters et al., Observations upon a compound of mustard gas and kerateine. Biochem J. 1947;41(4):550-5.
Peyton et al., Halofuginone infused keratin hydrogel attenuates adhesions in a rodent cecal abrasion model. J Surg Res. Dec. 2012;178(2):545-52.
Saul et al., Keratin hydrogels support the sustained release of bioactive ciprofloxacin. J Biomed Mater Res A. Sep. 15, 2011;98(4):544-53.
Science gateway, Tools: Centrifuge Rotor Speed Calculator. Retrieved online at: http://www.sciencegateway.org/tools/rotor.htm, 1 page, retrieved Aug. 23, 2016.
Sierpinski et al., the use of keratin biomaterials derived from human hair for the promotion of rapid regeneration of peripheral nerves. Biomaterials. 2008;29(1):118-28.
Thermo Scientific, Sorvall Evolution RC, Superspeed Centrifuge. www.thermoscientific.com/superspeedsolutions. 8 pages, (2007).
ThermoFisher Scientific, Dialysis Methods for Protein Research. Retrieved online at: https://www.thermofisher.com/us/en/home/life-science/protein-biology/prot- ein-biology-learning-center/protein-biology-resource-library/pierce-protei- n-methods/dialysis-methods-protein-research.html. 9 pages, retrieved Sep. 7, 2017.
International Search Report for Application No. PCT/US2013/068724, dated Feb. 24, 2014, 4 pages.
Supplementary European Search Report for Application No. 13853428.4, dated Jun. 24, 2016, 9 pages.

* cited by examiner

A.
2% KSOA
4% KSOA
5% KSOA
7% KSOA
10% KSOA
15% KSOA

B.

LOW PROTEIN PERCENTAGE GELLING COMPOSITIONS

1. FIELD OF THE INVENTION

This invention relates to compositions of keratin protein-based biomaterials and methods of making thereof.

2. BACKGROUND OF THE INVENTION

Keratins are a family of proteins found in the hair, skin, and other tissues of vertebrates. Hair is a unique source of human keratins because it is one of the few human tissues that are readily available and inexpensive. Although other sources of keratins are acceptable feedstocks for the present invention (e.g. wool, fur, horns, hooves, beaks, feathers, scales, and the like), human hair is preferred because of its biocompatibility in human medical applications.

Keratins can be extracted from human hair fibers by oxidation or reduction using methods that have been widely published in the art. If one employs a reductive treatment, the resulting keratins are referred to as kerateines. If an oxidative treatment is used, the resulting keratins are referred to as keratoses. These methods typically employ a two-step process whereby the crosslinked structure of keratins is broken down by either oxidation or reduction. In these reactions, the disulfide bonds in cystine amino acid residues are cleaved, rendering the keratins soluble without appreciable disruption of amide bonds. Many of the keratins can remain trapped within the cuticle's protective structure, so a second-step using a denaturing solution is typically employed to effect efficient extraction of the cortical proteins (alternatively, in the case of oxidation reactions, these steps can be combined). This step has also been widely published in the art as solutions such as urea, transition metal hydroxides, surfactant solutions, and combinations thereof have been employed. Common methods employ the use of aqueous solutions of tris(hydroxymethyl) aminomethane in concentrations between 0.1 and 1.0M, and urea solutions between 0.1 and 10M.

When oxidation is selected as the extraction method of choice, strong oxidants are used to cleave the cystine amino acid and solubilize the keratin proteins. A preferred oxidant is peracetic acid. Peracetic acid ($CH_3COOOH$) hydrolyzes into acetic acid ($CH_3COOH$) and hydrogen peroxide ($H_2O_2$). It also undergoes homolysis to produce peroxyl ($CH_3COO^-$; $CH_3COOO^-$), hydrogen (Fr), and hydroxyl ($HO^-$) radicals. Hydroxyl radicals are very strong oxidizing agents due to their high standard reduction potential (2310 mV). When reacted with $HO^-$, proteins decompose into fragments with carbonyl groups (—C=O) in the presence of oxygen ($O_2$) and a small fraction forms protein aggregates via cross-linking. Both of these degraded and cross-linked forms are observed in keratose samples. Aside from oxidation of cystine, peracetic acid (most likely through the action of $HO^-$ and $H_2O_2$)) also reacts and modifies other amino acids of the protein chain. The free thiols (—SH) of cysteines are converted to sulfenic acid (—SOH), which are further oxidized into sulfinic (—$SO_2H$) and sulfonic acid derivatives.

The ability to form a polymerized hydrogel is an important feature in biomaterials used as scaffolds for cells, agents for drug delivery or constructs to promote cell infiltration and tissue remodeling. Hydration of lyophilized keratose materials generally yields the formation of an elastic solid-like hydrogel at high solute concentrations (200 mg/ml in PBS). Rheological properties of these gels as well as their chemistries indicate that the primary mechanism of gelation is through polymer chain entanglement. Oxidation of free thiols eliminates the ability of oxidized keratins to reassemble via covalent disulfide bonding. Instead, other gelation determinant factors may include electrostatic and hydrophobic interaction. Keratin multimers may form a larger network through electrostatic attraction as suggested in the assembly of intermediate filament molecules in which the head (positive) and the tail (negative) domains of dimers potentially associate to form a tetramer. The negatively-charged sulfonic acid groups can also interact with the basic amino acid residues such as lysine, arginine, and histidine that escaped oxidation. Additionally, the coil regions of keratins that are rich in hydrophobic sequences may aggregate together to increase the polymer molecular weight and promote gelation.

Previously described compositions of keratin-based hydrogels have been reported. However, many of the hydrogels rely on relatively high protein percentages to establish and maintain the structure of the hydrogel. Accordingly, there is a great need to prepare compositions that form and maintain hydrogels at low protein percentages.

3. SUMMARY OF THE INVENTION

Disclosed herein are compositions of keratin-based biomaterials that form hydrogels at low protein percentages and uses thereof.

Also disclosed herein are compositions, and methods of making compositions, comprising keratose, keratein, or a combination thereof, wherein said composition forms a hydrogel at a protein concentration of less than 20%.

4. BRIEF DESCRIPTION OF THE FIGURES

Figure 1:
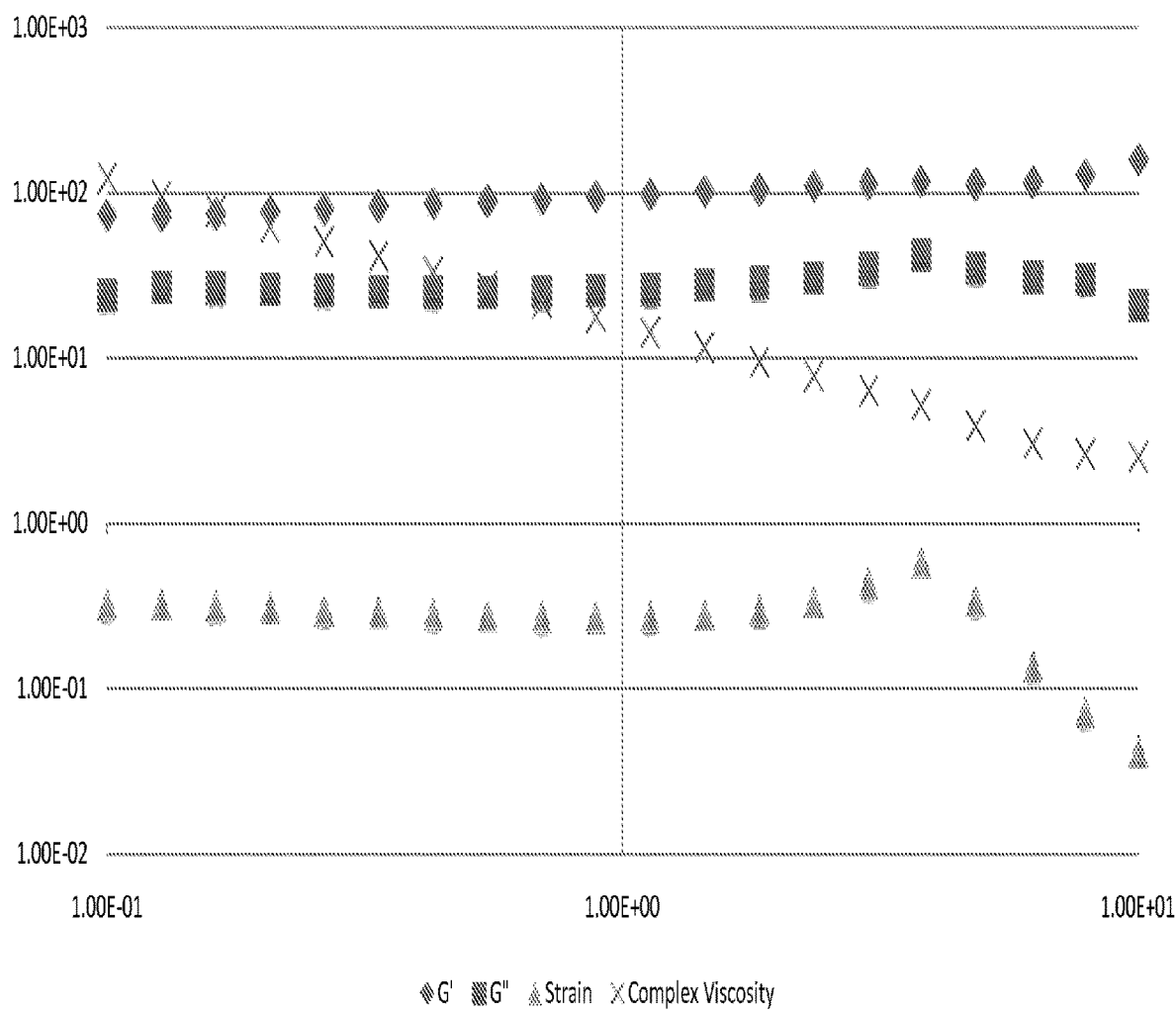
FIG. 1 depicts the rheological properties of 10% keratose samples that behave as hydrogels. These data show that 10% keratose samples exhibit hydrogel properties as they exhibit constant G' and G" values as the frequency is varied.
Figure 2:
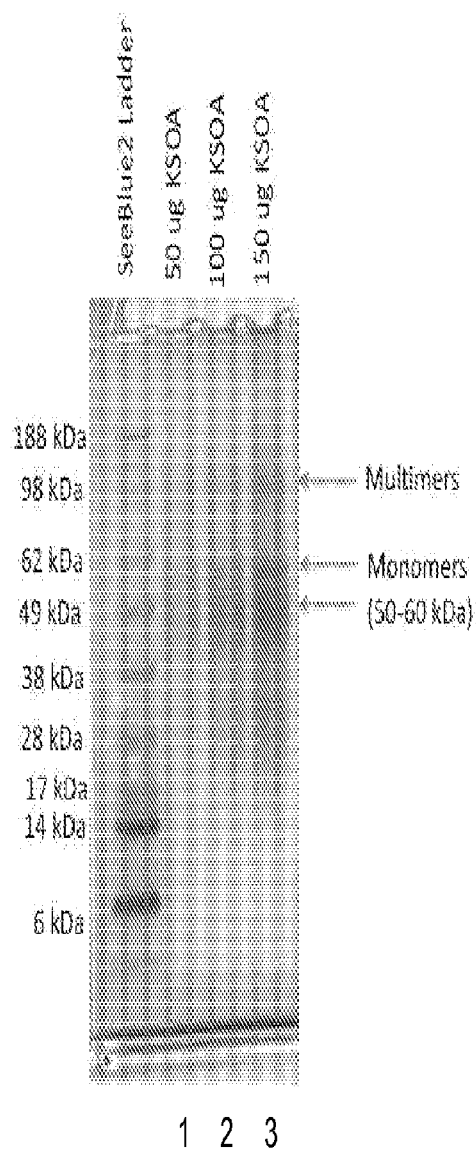
FIG. 2 depicts SDS-polyacrylamide gel representing alpha-keratose preparations at three different loading concentrations (50/100/150 μg/lane).
Figure 3:
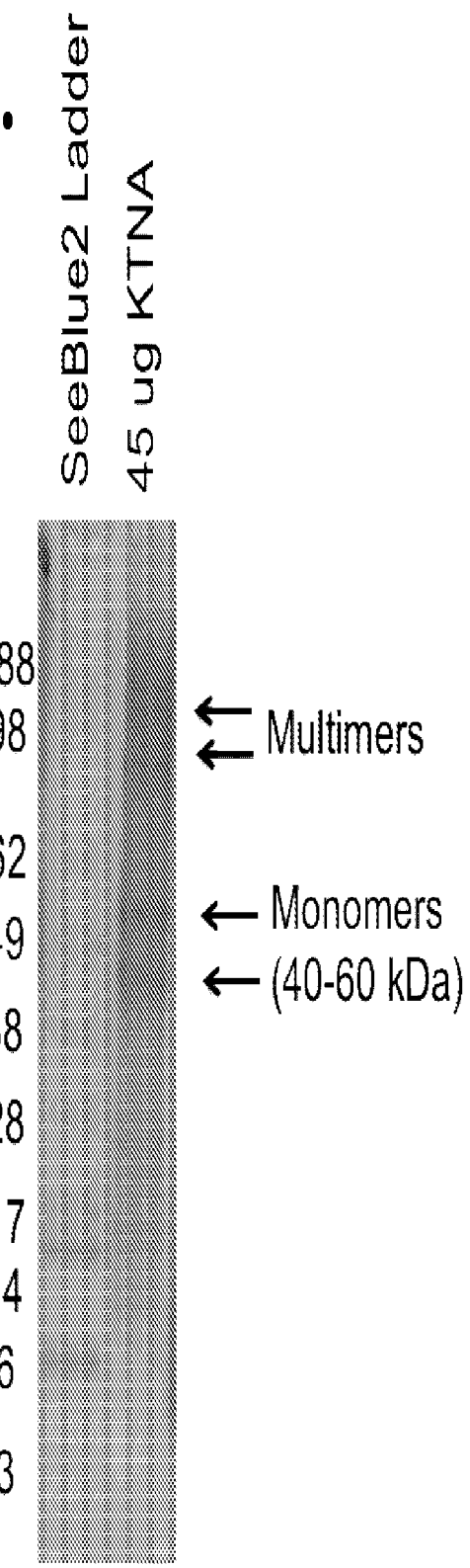

FIG. 3 Alpha-kerateine (KTNA) was subjected to SDS-PAGE analysis at a loading concentration of 45 μg/lane. The image of the gel indicates the high purity of the sample and the presence of different species of multimers of kerateine present in the same. The multimers present are not disrupted by the SDS-PAGE analysis.

Figure 4:
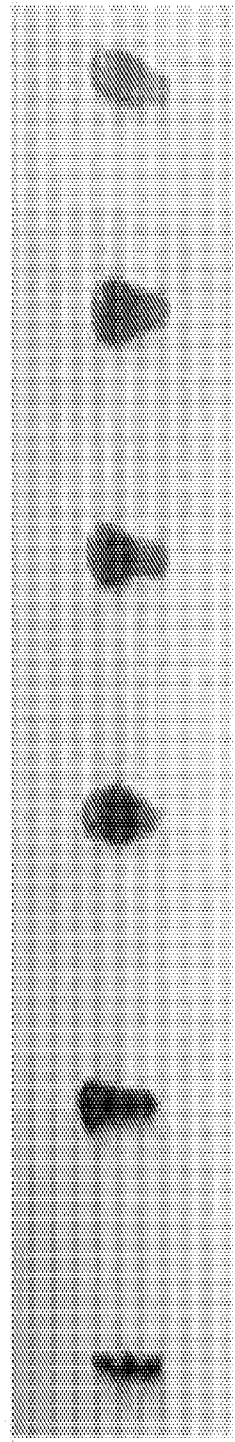
Figure 4:
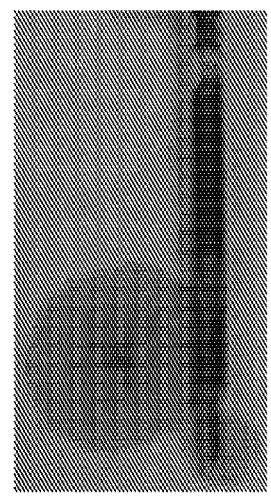

FIG. 4 represents the results from a gelation assay with alpha-keratose samples prepared as described herein. Hydrogels are formed at 2%, 4%, 7%, 10%, and 15% alpha-keratose (A., KSOA=alpha-keratose). Presented in B is an example of a keratose sample that has failed the gelation assay for comparison.

5. DETAILED DESCRIPTION

"Keratin protein source" as used herein includes proteinaceous sources of keratin proteins including but not limited to human or animal hair, wool, fur, horns, hooves, beaks, feathers, scales, and the like.

"Keratin protein(s)" as used herein collectively refers to keratin in keratin protein sources, including but not limited to naturally occurring keratin, reduced keratin, and/or oxidized keratin, or S-sulfonated keratin. This term also refers to the extracted keratin derivatives that are produced by oxidative and/or reductive treatment of keratin, including but not limited to keratose, alpha-keratose, gamma-keratose, kerateins, alpha-kerateine, or gamma-kerateine.

Keratin Protein Sources

Keratins are a family of proteins found in the hair, skin, and other tissues of vertebrates. Hair is a common source of human keratins because it is one of the few human tissues that are readily available and inexpensive. Other sources of keratins are acceptable feedstocks for the present invention, (e.g., wool, fur, horns, hooves, beaks, feathers, scales, and the like). Human hair is often used with human subjects because of its biocompatibility. Accordingly, in some embodiments, human hair is the keratin protein source. The human hair can be end-cut, as one would typically find in a barber shop or salon.

Keratin Proteins

Soluble keratins can be extracted from human hair fibers by oxidation or reduction using methods known in the art. These methods typically employ a two-step process whereby the crosslinked structure of keratins is broken down by either oxidation or reduction. In these reactions, the disulfide bonds in cystine amino acid residues are cleaved, rendering the keratins soluble. The cuticle is essentially unaffected by this treatment, so the majority of the keratins remain trapped within the cuticle's protective structure. In order to extract these keratins, a second step using a denaturing solution is employed. Alternatively, in the case of reduction reactions, these steps can be combined. Denaturing solutions known in the art include urea, transition metal hydroxides, surfactant solutions, and combinations thereof. Common methods use aqueous solutions of tris base (2-Amino-2-(hydroxymethyl)-1,3-propanediol) in concentrations between 0.1 and 1.0 M, and urea solutions between 0.1 and 10M, for oxidation and reduction reactions, respectively.

If one employs an oxidative treatment, the resulting keratins are referred to as "keratoses." If a reductive treatment is used, the resulting keratins are referred to as "kerateins."

Crude (unfractionated) extracts of keratins, regardless of redox state, can be further refined into matrix (KAP and gamma), alpha, and/or charged (acidic or basic) fractions by a variety of methods such as isoelectric precipitation, dialysis, or high performance liquid chromatography (HPLC), as desired. In a crude extract, the alpha fraction begins to precipitate below pH 6 and is essentially completely precipitated by pH 4.2.

In some embodiments, KAP co-precipitate with the alpha fraction, thereby producing an alpha/KAP mixture.

High molecular weight keratins, or "alpha keratins," (alpha helical), are thought to originate from the microfibrillar regions of the hair follicle, and typically range in molecular weight from about 40-85 kiloDaltons. Low molecular weight keratins, or "gamma keratins," or keratin-associated proteins (KAPs, globular), are thought to originate from the matrix regions of the hair follicle, and typically range in molecular weight from about 3-30 kiloDaltons for KAP and 10-15 kiloDaltons for gamma keratins.

In some embodiments, the keratin preparations (particularly alpha-keratose or alpha-kerateine) have average monomeric molecular weights of from about 45 to about 70 kiloDaltons. Gamma-keratoses and Gamma-kerateines have average molecular weights between 10 and 25 kiloDaltons and form complexes with alpha keratins. The alpha keratins extracted and described herein exist as obligate heterodimers that are complexed alpha keratin monomers with higher average molecular weights, e.g., up to 100 or 200 or 300 or 400 or 500 kiloDaltons. These combinations when complexed (e.g. alpha keratose, gamma keratose, alpha kerateine, gamma kerateine or combinations thereof) are termed "metakeratins".

Even though alpha and gamma keratins possess unique properties, the properties of subfamilies of both alpha and gamma keratins can only be revealed through more sophisticated means of purification and separation such as provided herein. Additional properties that are beneficial emerge and can be optimized upon further separation and purification of crude keratin extracts.

Keratose Production

One method for the production of keratoses is by oxidation of keratin with hydrogen peroxide, peracetic acid, or performic acid. In a specific embodiment, the oxidant is peracetic acid. Generally, a solution of peracetic acid is used at a concentration range of about 1% to about 10%. A specific concentration used can be a 2% solution of peracetic acid. In some embodiments, the oxidant concentrations range from a ratio of about 5:1 to about 50:1 weight to weight to the keratin protein source to be extracted. A specific embodiment uses a weight to weight ratio of 25:1 of a 2% peracetic acid solution. Those skilled in the art will recognize that slight modifications to the concentration can be made to affect varying degrees of oxidation, with concomitant alterations in reaction time, temperature, and liquid to solid ratio. It has also been discussed by Crewther et al. that performic acid offers the advantage of minimal peptide bond cleavage compared to peracetic acid. However, peracetic acid offers the advantages of cost and availability. In some embodiments, the oxidation temperature is between 0 and 100° Celsius. In a specific embodiment, the oxidation temperature is 37° C. In some embodiments, the oxidation time is between 0.5 and 24 hours. In a specific embodiment, the oxidation time is 12 hours. In some embodiments, mechanical mixing is used to maximize oxidation efficiency. Additional yield can be achieved with subsequent extractions with dilute solutions of oxidant, or water. After oxidation, the keratin protein source can be rinsed free of residual oxidant using purified water. In some embodiments, the oxidized keratin protein source is washed with water until residual oxidant is removed. In some embodiments, the washing step is performed until the washed keratin protein source does not test positive for oxidant.

The keratoses may be extracted from the oxidized keratin protein source using an aqueous solution of a denaturing agent. Protein denaturants are well known in the art, including but not limited to, urea, transition metal hydroxides (e.g. sodium and potassium hydroxide), ammonium hydroxide, and tris(hydroxymethyl)aminomethane (Tris, also known as Trizma® base). In some embodiments, Tris is used at a ratio of about 5:1 to about 50:1 weight of protein source, to a Tris solution of a concentration of about 0.01 to 1M. In a specific embodiment, the ratio is 25:1. In another specific embodiment, Tris is used at a concentration of 100 mM. Those skilled in the art will recognize that slight modifications to the concentration can be made to effect varying degrees of extraction, with concomitant alterations in reaction time, temperature, and liquid to solid ratio. In some embodiments, the extraction temperature is between 0° and 100° C. In a specific embodiment, the extraction temperature is 37° C. In some embodiments, the extraction time is between 0.5 and 24 hours. In a specific embodiment, the extraction time is about 2 hours. Additional yield can be achieved with subsequent extractions with dilute solutions of Tris or purified water. Often, the extraction is performed with mechanical agitation in a mixing tank to ensure a more efficient yield.

Kerateine Production

Similar to the methods described above for extraction and purification of keratoses, kerateines can be produced by reduction of a keratin protein source with thioglycolic acid or beta-mercaptoethanol. Specifically, thioglycolic acid (TGA) is often used. In some embodiments, TGA is added to the keratin protein source at a ratio of about 5:1 to about 50:1. In a specific embodiment, TGA is added at a ratio of 25:1. The TGA is added at a solution ranging in concentrations from about 0.1 to about 10M. In a specific embodiment, the TGA is added in solution at a concentration of 0.5M. During extraction, mechanical agitation is used to maximize extraction efficiency.

The solution containing reductant and extracted kerateine proteins (soluble keratin protein solution) is the collected and stored by straining the keratin protein source through a 400 micron mesh and storing the solution at 4° C. A base is then added to the drained keratin protein source in a ratio of about 10:1 to about 50:1. In a specific embodiment, the base is added to the drained keratin protein source at a ratio of 25:1. In some embodiments, the base is Tris generally used at a concentration of about 100 mM. The keratin protein source in the solution with base is mixed with agitation of about 2 hours at 37° C. The solution containing the base and extracted keratin proteins (soluble keratin protein solution) is then filtered through a added to the first extracted solution and stored Those skilled in the art will recognize that slight modifications to the concentration can be made to effect varying degree of reduction, with concomitant alterations in pH, reaction time, temperature, and liquid to solid ratio. In some embodiments, the reduction is performed at a temperature between 0 and 100° C. In a specific embodiment, the temperature is 37° C. In some embodiments, the reduction time is between 0.5 and 24 hours. In a specific embodiment, the reduction is performed for 15 hours. Unlike the previously described oxidation reaction, reduction is carried out at basic pH. Keratins are highly soluble in a reduction media and are expected to be extracted. The reduction solution may therefore be combined with the subsequent extraction solutions and processed accordingly. The reduction is carried out with mechanical agitation in a mixing tank to increase the efficiency of the reduction of the keratin proteins.

Residual reductant and denaturing agents can be removed from solution by dialysis. Typical dialysis conditions are 1 to 2% solution of kerateines dialyzed against purified water. Those skilled in the art will recognize that other methods exist for the removal of low molecular weight contaminants in addition to dialysis (e.g. microfiltration, chromatography, and the like). Once dissolved, the kerateines are stable in solution without the denaturing agent for finite periods. Therefore, the denaturing agent can be removed without the resultant precipitation of kerateines. Regardless of the fractionation/purification process, the resulting kerateines can be concentrated and lyophilized, similar to keratoses.

A soluble keratin protein solution is produced by the extraction of keratose and/or kerateine by either oxidative means for keratose, or by reductive means for kerateine.

High Speed Centrifugation

In order to remove many of the keratin associated proteins and other proteins extracted through either oxidative or reductive processes listed above, a high speed centrifugation step is used. Current methods known in the art generally use a low speed centrifugation (around 4,000 rpm) to clear particulate matter. However, this speed does not create enough force to remove many of the beta keratin protein contaminants present in the extracted protein solution. Thus, in some embodiments, high speed centrifugation is employed. Speeds in excess of about 5,000 rpm to about 30,000 rpm can be used. In a specific embodiment, the extracted protein solution is spun at about 20,000 rpm to produce a clarified protein solution of solubilized keratin proteins. In another specific embodiment, the high speed centrifugation step is performed at about 4° C.

A clarified protein solution is produced by the high speed centrifugation of the soluble keratin protein solution.

Dialysis

In many instances during protein purification, dialysis is used to separate or even to concentrate certain protein species present in the sample. Accordingly here, in many embodiments, the clarified protein solution is subjected to a dialysis step to fractionate certain protein species. In some embodiments, a 100 kDa molecular weight cutoff membrane is employed in the purification of alpha-keratose or alpha-kerateine. In other embodiments, a 5 kDa molecular weight cutoff membrane is employed to purify gamma-keratose or gamma kerateine. A common matrix for the dialysis membranes is regenerated cellulose, however, many other membrane preparations suitable for protein purification may be used.

In many instances, pressure is applied to aid in the dialysis process. If the pressure applied is too low, the resultant solutions contain greater protein fragments and peptides. Conversely, if the pressure is too high, the result is protein complex degradation. Thus, in some embodiments, the dialysis is performed under conditions that maintain a transmembrane pressure from about 30 to about 70 psi. In some embodiments the transmembrane pressure is about 30 to about 40 psi, in others it is about 60 to about 70 psi. Further, it is important to minimize the heat buildup developed by the shear stress of pressurized dialysis. Thus, in some embodiments, the dialysis is carried out at a temperature from about 4° C. to about 20° C. In a specific embodiment, the dialysis is carried out at about 15° C.

Additionally, as the solution is dialyzed, the conductivity is adjusted. In some embodiments, the conductivity is adjusted down to about or below 0.6 mS. In some instances, the conductivity is adjusted with water.

Lyophilization

Storage of proteins for any length of time can pose stability problems. Since proteins are generally more stable at colder temperatures, maintenance at low temperatures even for short duration is recommended. Typically, proteins can be freeze-dried (lyophilized) to achieve storage conditions while maintaining protein stability.

In some embodiments, lyophilization is used to produce a protein cake of purified protein. The lyophilization is used to stabilize the extracted keratin proteins. Methods known in the art such as shell freezing followed by vacuum or bulk freezing and applying high heat tend to degrade proteins. Accordingly, in some embodiments, a keratin protein cake, comprising keratose alpha or gamma and/or kerateine alpha or gamma is produced by a lyophilization of a clarified keratin protein solution, optionally after dialysis.

In some embodiments, the clarified protein solution post-dialysis is bulk frozen at about −40° C., and then a vacuum is applied until the containment containing the solution reaches about 250 torr. In some embodiments, heat is then applied in a step-wise fashion, bringing the material to about 0° C., then to about 25° C., then to about 37° C., while maintaining 250 torr pressure. In some embodiments, the lyophilization process occurs over a 24 hour period.

Grinding

Precise grinding of the lyophilized material aids in the homogeneity of reconstitution and protein stability. Previous methods involve crude grinding methods, including grinding or chopping of the material in a laboratory blender. In the present invention, some embodiments employ a commercial grinding apparatus to machine the material to a homogenous particle size. In some embodiments, a pharmaceutical mill is employed. In other embodiments, the particle size is about 1000 microns or less in diameter.

It is also important to remove the static charge from the ground material to make it easier to work with. Accordingly, in some embodiments, the ground material has been deionized.

Hydrogel Preparation

Hydrogels were prepared for analysis by carefully weighing the appropriate keratin lyophilized powder or powders. The powders were diluted in either sterile phosphobuffer saline or sterile water to generate the described percent mass to volume ratio. These solutions were placed in a 37° C. incubator overnight before analysis.

In some embodiments, the hydrogel comprises less than 20% protein in a weight to volume ratio. In other embodiments, the hydrogels comprise less than 19% protein, less than 18%, less than 17%, less than 16%, less than 15%, less than 14%, less than 13%, less than 12%, less than 11%, less than 10%, less than 9%, less than 8%, less than 7%, less than 6%, less than 5%, less than 4% protein, or less than 3% in a weight to volume ratio.

In other embodiments, the hydrogel comprises about 2%, about 3%, about 4%, about 5%, about 6%, about 7%, about 8%, about 9%, about 10%, about 11%, about 12%, about 13%, about 14%, about 15%, about 16%, about 17%, about 18%, or about 19% protein in a weight to volume ratio. Inother embodiments, the hydrogel comprises 2%, 3%, 4%, 5%, 6%, 7%, 8%, 9%, 10%, 11%, 12%, 13%, 14%, 15%, 16%, 17%, 18%, or 19% protein in a weight to volume ratio.

In some embodiments, the hydrogel may comprise 80%, 85%, 90%, 95%, 99% or more keratose. The keratose may be alpha-keratose or gamma-keratose, or some combination thereof. In some embodiments, the keratose in the hydrogel comprises 50%, 55%, 60%, 65%, 70%, 75%, 80%, 85%, 90%, 95%, 99% or more alpha-keratose. In other embodiments, the hydrogel comprises 50%, 55%, 60%, 65%, 70%, 75%, 80%, 85%, 90%, 95%, 99% or more gamma-keratose. In alternative embodiments, the hydrogel is substantially free of gamma-keratose. In some embodiments, the hydrogel is substantially free of kerateine. In other embodiments, keratose-based hydrogels are substantially free of disulfide bonds.

In some embodiments, the hydrogel may comprise 80%, 85%, 90%, 95%, 99% or more kerateine. The kerateine may be alpha-kerateine or gamma-kerateine, or some combination thereof. In some embodiments, the kerateine in the hydrogel comprises 50%, 55%, 60%, 65%, 70%, 75%, 80%, 85%, 90%, 95%, 99% or more alpha-kerateine. In other embodiments, the hydrogel comprises 50%, 55%, 60%, 65%, 70%, 75%, 80%, 85%, 90%, 95%, 99% or more gamma-kerateine. In alternative embodiments, the hydrogel is substantially free of gamma-kerateine. In other embodiments, the hydrogel is substantially free of alpha or gamma kerateine.

In yet other embodiments, the hydrogels described herein present similar gelation and stability properties of gels of higher percentage protein concentration then have been reported. In some embodiments, compositions of the invention comprise hydrogels of less than 20% protein that exhibit similar gelation and/or stability properties than hydrogels reported in the art that comprise 20% or more protein. In other embodiments, compositions of the invention comprise hydrogels of less than 20% protein that exhibit superior gelation and/or stability properties than hydrogels reported in the art that comprise 20% or more protein.

In other embodiments, methods of the invention comprise making hydrogels of less than 20% protein. Preparing a hydrogel is described above by may comprise the following steps: a) providing keratose, kerateine, or a combination thereof, at a concentration of less than 20% weight to volume in an aqueous medium; b) mixing said keratose, kerateine, or a combination thereof in said aqueous medium; and c) allowing the hydrogel to form. Sometimes, the keratose, kerateine, or a combination thereof has previously been lyophilized. Also, the keratose, kerateine or a combination thereof is provided as a ground protein powder.

Also, the hydrogels described herein do not require additional biomaterials or added crosslinkers to create or maintain structure. Thus, the compositions presented herein are substantially free of added biomaterials or crosslinkers. Such biomaterials and or crosslinkers include, but are not limited to: albumin, (hydroxyethyl)starch, poly-aspartamide, poly(vinyl alcohol), hyaluronic acid, alginate, chitosan, collagen, gelatin, fibrin, silk, poly(ethylene glycol) (aka PEG), poly(lactic acid) (aka PLA), poly(lactic-co-glycolic acid) (aka PLGA), poly(glycolic acid) (aka PGA), poly(dioxanone), poly(caprolacetone), poly(PCPP-SA anhydride), poly(2-hydroxyethyl methacrylate) (aka pHEMA), dextran, dextran plus glycidylmethacrylate (GMA), cylcodextran, dioleyl phosphatidylethanolamine (DOPE) and other catatonic lipids forming nanoparticles, calcium sulphates (bone powders/pastes), glutaraldehyde, 1-ethyl-3-(3-dimethylaminopropyl) carbodiimide) (aka EDC), methylenebsacrylamide, hexamethylenediisocyanate, 1,4-bis (acryloyl)piperazine, 1,4-cyclohexanedimethanol divinyl ether, 1,4-phenylenediacryloyl chloride, 1,6-hexanediol diacrylate, N-(1-hydroxy-2,2-dimethoxyethyl)acrylamide, di(ethylene glycol) diacrylate, di(ethylene glycol) dimethacrylate, ethylene glycol diacrylate, ethylene glycol dimethacrylate, divinylbenzene, genipin or other common biomaterials or crosslinking agents or agents that are used to bolster structure known in the art. Additional hydrogel forming compositions are described in U.S. Pat. No. 5,854, 382.

6. EXAMPLES

6.1 Example 1

Keratose Extraction Methods (Oxidative Extraction) and Preparation of Keratose Hydrogels Untreated Chinese hair was used in the extraction method. The hair was cut to lengths of ¼, ½, ¾ and 1 inch segments and washed in a warm water solution.

Step 1: The hair was added to a mixing tank. The tank was a vessel that contained a propeller for mechanical agitation. The oxidant was added to the vessel. The oxidant used was a 2% solution of peracetic acid (PAA) at a 25:1 weight-to-weight ratio. The mixture was mechanically mixed for a period of 12 hours at 37° C.

Step 2: The residual solution containing the oxidant was drained, neutralized and discarded.

Step 3: The oxidized hair was collected and rinsed with water until PAA test strips revealed no residual oxidant in the solution.

Step 4: A base was then added to the drained hair in a ratio of 25:1. In this Example, a 100 mM Tris base was used. The solution was mixed with mechanical agitation in the mixing tank for 2 hours at 37° C.

Step 5: The solution containing base and extracted keratin proteins was then collected and stored in a separate container at 4° C. The remaining hair was retained by sieving through a steel mesh with a pore size of the mesh of 400 microns.

Step 6: Purified water was then added to the hair at a ratio of 25:1 and mixed for 2 hours at 37° C.

were able to flow from the incubation tubes were measured in a 14 mm cup and bob apparatus. Solutions that were too complexed to flow were measured between a 20 mm plate and plate apparatus with a 15 mm gap. All measurements were performed at 25° C. Preliminary stress sweep test were performed on each sample to determine the linear region within the viscoelastic response. The frequency dependence of the viscoelastic properties of the keratose gels were measured at 25 Pa. The elastic modulus, viscous modulus, and complex viscosity were measured and reported in Table 1, below.

TABLE 1

| | Rheological values of keratose gels (n = 3) | | | | | |
|---|---|---|---|---|---|---|
| Frequency | 20% from de Guzeman et al. 2011 | | 10% | | 15% | |
| (Hz) | 0.1 | 1 | 0.1 | 1 | 0.1 | 1 |
| $G^*$ (Pa) | 164.94 +/− 86.19 | 215.70 +/− 91.30 | 72.0 +/− 7.4 | 95.7 +/− 3.9 | 675.9 +/− 34.6 | 811.0 +/− 2.7 |
| $G'$ (Pa) | 162.53 +/− 86.20 | 210.97 +/− 91.12 | 68.4 +/− 7.0 | 95.7 +/− 3.4 | 669.4 +/− 38.6 | 801.9 +/− 5.8 |
| $G''$ (Pa) | 27.48 +/− 7.40 | 44.22 +/− 10.48 | 22.4 +/− 2.4 | 25.1 +/− 1.5 | 889.8 +/− 28.9 | 119.0 +/− 22.7 |
| $\eta^*$ (Pas) | 262.53 +/− 137.22 | 34.33 +/− 14.57 | 114.5 +/− 11.7 | 13.9 +/− 0.6 | 1075.3 +/− 54.7 | 113.9 +/− 0.2 |

Step 7: The solution containing water and extracted keratin proteins was then collected and added to the solution from Step 5 in a separate container stored at 4° C. In order to get the maximum extraction yield, the hair was sieved through a steel mesh with a pore size of 400 microns.

Step 8: The combined mixture from Step 5 and Step 7 was then centrifuged at 20,000 rpm to remove any solids or beta-keratins.

Step 9: The centrifuged solution was filtered with a 20 micrometer pore size capsule filter.

Step 10: The solution from Step 9 was dialyzed against a 100 kDa molecular weight cut off dialysis membrane, made from regenerated cellulose, using standard tangential flow filtration. The solution was cooled to dissipate the heat from shear forces on pumps. Also, trans-membrane pressures were maintained between 30-40 psi during the dialysis process. The solution was dialyzed until the conductivity reached 0.6 mS using additions of purified water to replace permeate. The first complete solution wash was collected and stored in a storage tank at 4° C.

Step 11: The solution from Step 10 was then lyophilized into a keratin protein cake of alpha keratose. The solution was bulk frozen to −40° C. quickly then had a vacuum applied until the containment vessel containing the protein reached 250 torr. Heat was then applied in a step-wise fashion to bring the material first to 0° C., then to 25° C., then to 37° C. while maintaining 250 torr.

Step 12: The keratin protein cake from Step 12 was ground using a pharmaceutical mill with mesh sizes of 500 or 1000 microns. The ground protein was deionized to better allow further processing. The ground protein was then placed in sterile bags to be stored prior to reconstitution.

Preparation of Keratose Hydrogels

Keratose hydrogels were prepared for analysis by carefully weighing the appropriate keratin lyophilized powder. The powders were diluted in either sterile phosphobuffer saline or sterile water to generate the described percent mass to volume ratio. These solutions were placed in a 37° C. incubator overnight before analysis.

For rheological data, two measurements were performed on a Bohlin CS-10 Rotational Rheometer. Solutions that Presented in Table 1 are the rheological values for a 20% keratose gel from de Guzeman et al. 2011 (lanes 1 and 2), and keratose hydrogels prepared as in this example at 10% keratose (lanes 3 and 4) and at 15% (lanes 5 and 6). Of note, the rheological data reported from de Guzeman et al. demonstrated very high standard deviations versus the values for all the materials tested from the material described herein. The high variability in the gels reported from de Guzeman suggests that the structure is not uniform throughout the different samples. Conversely, the data for 10% gels prepared as presented herein produces very small standard deviations when the various rheological parameters are tested. The 10% keratose gels exhibited a very low standard deviation in measurements for dynamic complex modulus ($G^*$), dynamic elastic/storage modulus ($G'$), dynamic complex viscosity ($\eta^*$), and dynamic viscous/loss modulus ($G''$). These data demonstrated that the 10% hydrogels produced herein exhibit a more uniform, stable structure than the 20% gels reported in the art. Further, the data for 15% gels prepared as presented herein exhibited very small standard deviations when the various rheological parameters are tested. The 15% keratose gels exhibited a very low standard deviation in measurements for dynamic complex modulus, dynamic elastic/storage modulus, dynamic complex viscosity, and dynamic viscous/loss modulus. These data demonstrate that the 15% hydrogels produced herein also exhibit a more uniform, stable structure than the 20% gels reported in the art.

6.2 Example 2

Kerateine Extraction Methods (Reductive Extraction) and Preparation of Kerateine Hydrogels Untreated Chinese hair was end-cut to lengths of ¼, ½, ¾ and 1 inch segments and washed in a warm water solution.

Step 1: The hair was added to a vessel that contained a propeller for mechanical agitation. The reductant was added to the vessel. The reductant was a 0.5M solution of a thioglycolic acid (TGA) at a ratio of 25:1. The mixture was mechanically mixed for a period of 15 hours at 37° C.

Step 2: The solution containing reductant and extracted keratin proteins was collected and stored in a separate container at 4° C. The remaining hair was retained by sieving through a steel mesh with a pore size of 400 microns.

Step 3: A base was then added to the drained hair in a ratio of 25:1. The base used here was a 100 mM Tris base solution. The solution was mixed with mechanical agitation in a mixing tank for 2 hours at 37° C.

Step 4: The solution containing base and extracted keratin proteins was collected and added to the solution from Step 2 and stored at 4° C. The remaining hair was retained by sieving through a steel mesh with a pore size of 400 microns.

Step 5: Purified water was added to the hair at a ratio of 25:1 and mixed for 2 hours at 37° C.

Step 6: The solution containing water and extracted keratin proteins was collected as in Step 4 and added to the solution from Step 4 and stored at 4° C. Sterile water was added to the hair at a ratio of 40:1 and mixed for 2 hours at 37° C.

Step 7: A second reduction step was needed to fully extract the keratin proteins from the hair shaft. The reductant used was a 0.5M solution of a thioglycolic acid (TGA) at a ratio of 25:1. The mixture was mechanically mixed for a period of 15 hours at 37° C.

Step 8: The solution containing reductant and extracted keratin proteins was collected and stored in a separate vessel containing the solution from Step 6 and stored at 4° C. The remaining hair was retained by sieving through a steel mesh with a pore size of 400 microns. Mechanical agitation applied during the straining process helps to strain as much solution from the hair mass.

Step 9: A base was added to the drained hair in a ratio of 25:1. The base used was a 100 mM Tris base solution. The solution was mixed with mechanical agitation in a mixing tank for 2 hours at 37° C.

Step 10: The solution containing base and extracted keratin proteins was then collected and added to the solution from Step 8 and stored at 4° C. The remaining hair was retained by sieving through a steel mesh with a pore size of 400 microns. Mechanical agitation applied during the straining process helps to strain as much solution as possible from the hair mass.

Step 11: Purified water was then added to the hair at a ratio of 10:1 and mixed for 2 hours at 37° C.

Step 12: The solution containing water and extracted keratin proteins was collected and added to the solution from Step 10 stored at 4° C. In order to get the maximum extraction yield, the hair was sieved through a steel mesh of a pore size of 400 microns.

Step 13: The combined mixture from Steps 12, 10, 8, 6, 4, and 2 was centrifuged at 20,000 rpm to remove any solids or beta keratins.

Step 14: The centrifuged solution was filtered with a 20 micrometer pore size capsule filter.

Step 15: The solution from Step 14 was dialyzed against a 100 kDa molecular weight cut off regenerated cellulose dialysis membrane using standard tangential flow filtration methods. The solution was cooled to dissipate the heat from shear forces on pumps. Also, trans-membrane pressures were maintained between 50-60 psi during the dialysis process. The solution was dialyzed until the conductivity lowered from about 24 mS to about 0.6 mS using additions of purified water to replace permeate. This required about 5 complete volume changes (or washes) and left some residual TGA in the solution. The TGA was completely removed by dialyzing until the conductivity reached 0 mS or 12-20 volume changes.

Step 16: The solution from Step 15 was lyophilized into a keratin protein cake of alpha kerateine. Here, the lyophilization step was to bulk freeze the solution to −40° C. quickly then apply a vacuum until the containment vessel containing the protein reached 250 torr. Heat was applied in a step-wise fashion to bring the material first to 0° C., then to 25° C., then to 37° C. while maintaining 250 torr. The temperature was not allowed to exceed 37° C. in order to prevent degradation during the drying process.

Step 17: The keratin protein cake from Step 16 was ground using a pharmaceutical mill with a mesh size of 500 or 1000 microns. The ground protein was deionized to better allow further processing. The ground protein was then placed in sterile bags and stored until reconstitution.

Production of Kerateine Hydrogels

Kerateine hydrogels were prepared for analysis by carefully weighing the appropriate keratin lyophilized powder. The powders were diluted in sterile water to generate the described percent mass to volume ratio. These solutions were placed in a 37° C. incubator overnight before analysis.

For rheological data, measurements were performed on a Bohlin CS-10 Rotational Rheometer. Solutions that were able to flow from the incubation tubes were measured in a 14 mm cup and bob apparatus. Solutions that were too complexed to flow were measured between a 20 mm plate and plate apparatus with a 15 mm gap. All measurements were performed at 25° C. Preliminary stress sweep test were performed on each sample to determine the linear region within the viscoelastic response. The frequency dependence of the viscoelastic properties of the kerateine gels were measured at 25 Pa. The elastic modulus, viscous modulus, and complex viscosity were measured and reported in Tables 2 and 3, below.

TABLE 2

Rheological values of kerateine gels (n = 3)

| | 20% from Richter et al. 2011 | 8% | 20% |
|---|---|---|---|
| Frequency (Hz) | 1 | 1 | 1 |
| G'(Pa) | 8870 +/− 580 | 1590 +/− 1454 | 19408 +/− 5314.5 |
| G"(Pa) | 550 +/− 20 | 45.3 +/− 33.0 | 1663.8 +/− 621.6 |
| η*(Pa) | 87.8 +/− 3.6 | 223.6 +/− 204.4 | 2738.6 +/− 751.8 |

Presented in Table 2 are the rheological values for a 20% kerateine gel from Richter et al. 2011 (lane 1), and kerateine hydrogels prepared as in this example at 8% kerateine (lane 2) and at 20% (lane 3). Of note, the rheological data reported from Richter et al. demonstrated low standard deviations versus the real values for all the parameters tested. It is expected that the kerateine in the hydrogels retains free sulfhydryl groups capable of forming disulfide bonds at random. The random formation of disulfide bonds produces heterogeneity beyond complexing (as opposed to keratose hydrogels which rely solely on complexing to form structure). Thus, the heterogeneity in structure of the hydrogel leads to variable rheological data from sample to sample. Accordingly, the rheological data from a kerateine hydrogel should exhibit a high level of standard deviation. The relatively low variability in the gels reported from Richter suggests that the structure is very uniform throughout the different samples with less random disulfide bonding. Conversely, the data for 8% gels prepared as presented herein produce very high standard deviations when the various rheological parameters are tested. The 8% kerateine gels exhibited a high standard deviation in measurements for dynamic complex modulus (G*), dynamic elastic/storage modulus (G'), dynamic complex viscosity (η*), and dynamic viscous/loss modulus (G"). These data demonstrated that the 8% hydrogels produced herein exhibit a less uniform, but more stable structure with more random disulfide bonding than the 20% gels reported in the art. Further, the data for 20% gels prepared as presented herein exhibited very high standard deviations when the various rheological parameters are tested. The 20% kerateine gels exhibited a very high standard deviation in measurements for dynamic complex modulus (G*), dynamic elastic/storage modulus (G'), dynamic complex viscosity ($\eta$*), and dynamic viscous/loss modulus (G"). These data demonstrate that the 20% hydrogels produced herein also exhibit a less uniform, but more stable structure with more random disulfide bonding than the 20% gels reported in the art.

TABLE 3

Rheological values of kerateine gels (n = 3)

| | 20% from Richter et al. 2011 | 10% | 15% | 20% |
|---|---|---|---|---|
| Frequency (Hz) | 1 | 1 | 1 | 1 |
| G'(Pa) | 8870 +/− 580 | 3140 +/− 332 | 10680 +/− 1007 | 21816 +/− 6687 |
| G"(Pa) | 550 +/− 20 | 280 +/− 30 | 1716 +/− 88 | 4949 +/− 1843 |
| $\eta$*(Pas) | 87.8 +/− 3.6 | 443 +/− 47 | 1521 +/− 142 | 3145 +/− 967 |

Presented in Table 3 are the rheological values for a 20% kerateine gel from Richter et al. 2011 (lane 1), and kerateine hydrogels prepared as in this example at 10% kerateine (lane 2) and at 15% (lane 3) and at 20% (lane 3). Of note, the rheological data reported from Richter et al. demonstrated low standard deviations versus the real values for all the parameters tested. It is expected that the kerateine in the hydrogels retains free sulfhydryl groups capable of forming disulfide bonds at random. The random formation of disulfide bonds produces heterogeneity beyond complexing (as opposed to keratose hydrogels which rely solely on complexing to form structure). Thus, the heterogeneity in structure of the hydrogel leads to variable rheological data from sample to sample. Accordingly, the rheological data from a kerateine hydrogel should exhibit a high level of standard deviation. The relatively low variability in the gels reported from Richter suggests that the structure is very uniform throughout the different samples with less random disulfide bonding. Conversely, the data for 10% gels prepared as presented herein produce very high standard deviations when the various rheological parameters are tested. The 10% kerateine gels exhibited a very high standard deviation in measurements for dynamic complex modulus (G*), dynamic elastic/storage modulus (G'), dynamic complex viscosity ($\eta$*), and dynamic viscous/loss modulus (G"). These data demonstrated that the 10% hydrogels produced herein exhibit a less uniform, but more stable structure with more random disulfide bonding than the 20% gels reported in the art. Further, the data for 15% gels prepared as presented herein exhibited very high standard deviations when the various rheological parameters are tested. The 15% kerateine gels exhibited high standard deviations in measurements for dynamic complex modulus (G*), dynamic elastic/storage modulus (G'), dynamic complex viscosity ($\eta$*), and dynamic viscous/loss modulus (G"). These data demonstrate that the 15% hydrogels produced herein also exhibit a less uniform, but more stable structure with more random disulfide bonding than the 20% gels reported in the art. Moreover, the data for 20% gels prepared as presented herein exhibited very high standard deviations when the various rheological parameters are tested. The 20% kerateine gels exhibited a high standard deviation in measurements for dynamic complex modulus (G*), dynamic elastic/storage modulus (G'), dynamic complex viscosity ($\eta$*), and dynamic viscous/loss modulus (G"). These data demonstrate that the 20% hydrogels produced herein also exhibit a less uniform, but a more stable structure with more random disulfide bonding than the 20% gels reported in the art.

We claim:

1. A composition comprising keratose, kerateine or a combination thereof, wherein said composition forms a hydrogel at a protein concentration of less than 20%,
    wherein said keratose, kerateine or combination thereof is prepared by a method including dialyzing said keratose, kerateine or combination thereof at a transmembrane pressure of from about 30 psi to about 70 psi, and
    wherein said hydrogel exhibits a dynamic complex viscosity of at least 113.9 Pascals as measured at 25.degree. Celsius at a frequency of 1 Hertz.

2. The composition of claim 1, wherein said composition is substantially free of gamma-keratose or gamma-kerateine.

3. The composition of claim 1, wherein said composition is substantially free of biomaterial adjuncts or crosslinking agents.

4. The composition of claim 1, wherein said protein concentration is 15% or less.

5. The composition of claim 1, wherein said protein concentration is 10% or less.

6. The composition of claim 1, wherein said hydrogel is formed between about 25° C. and about 37° C.

7. The composition of claim 1, wherein said hydrogel is stable at about 25° C. to about 37° C.

8. The composition of claim 1, wherein total protein in said hydrogel comprises at least 90% or more keratose.

9. The composition of claim 8, wherein said hydrogel is substantially free of kerateine.

10. The composition of claim 8, wherein said hydrogel is substantially free of disulfide bonds.

11. The composition of claim 1, wherein total protein in said hydrogel comprises at least 90% or more kerateine.

12. The composition of claim 10, wherein said hydrogel is substantially free of keratose.

13. The composition of any of claim 1, wherein said keratose, kerateine or combination thereof is derived from a human keratin source.

14. The composition of claim 13, wherein said human keratin source is hair.

15. A method of forming a hydrogel comprising:
    a. providing keratose, kerateine, or a combination thereof, at a concentration of less than 20% weight to volume in an aqueous medium;
    b. mixing said keratose, kerateine, or a combination thereof in said aqueous medium; and
    c. allowing the hydrogel to form;
    wherein said keratose, keratein or combination thereof have been previously subjected to dialysis at a transmembrane pressure of from about 30 psi to about 70 psi.

16. The method of claim 15, wherein said keratose, kerateine, or a combination thereof have previously been lyophilized.

17. The method of claim 15, wherein said keratose, kerateine or combination thereof have been previously subjected to dialysis.

18. The method of claim 14, wherein said keratose, kerateine or a combination thereof is provided as a ground protein powder.

19. The composition of claim 1, wherein said transmembrane pressure is from about 30 psi to about 40 psi.

20. The composition of claim 1, wherein said transmembrane pressure is from about 60 psi to about 70 psi.

21. The method of claim 17, wherein said dialysis is carried out at a transmembrane pressure of from about 30 psi to about 70 psi.

22. The method of claim 17, wherein said dialysis is carried out at a transmembrane pressure of from about 30 psi to about 40 psi.

23. The method of claim 17, wherein said dialysis is carried out at a transmembrane pressure of from about 60 psi to about 70 psi.

24. The method of claim 17, wherein said dialysis is carried out at a temperature of from about 4° C. to about 20° C.

25. The composition of claim 1, wherein said dialysis is carried out at a temperature of from about 4° C. to about 20° C.

* * * * *